United States Patent [19]

Dumon

[11] Patent Number: 5,236,446

[45] Date of Patent: Aug. 17, 1993

[54] TUBULAR ENDOPROSTHESIS FOR ANATOMICAL CONDUITS

[76] Inventor: Jean-Francois Dumon, Clos d'Albizzi, 3, avenue de la Gare, Cassis, France, 13260

[21] Appl. No.: 566,350

[22] PCT Filed: Mar. 2, 1989

[86] PCT No.: PCT/FR89/00083

§ 371 Date: Aug. 23, 1990

§ 102(e) Date: Aug. 23, 1990

[87] PCT Pub. No.: WO89/07916

PCT Pub. Date: Sep. 8, 1989

[30] Foreign Application Priority Data

Mar. 2, 1988 [FR] France ................. 88 02835

[51] Int. Cl.$^5$ .............................. A61F 2/06
[52] U.S. Cl. ........................ 623/1; 606/151; 623/12; 604/53; 128/830
[58] Field of Search ............ 623/1, 8, 12, 4, 9, 623/11, 17; 604/53, 96, 264; 128/830-834, 842-844; 606/151

[56] References Cited

U.S. PATENT DOCUMENTS

| 2,701,559 | 2/1955 | Cooper | 128/2 |
| 3,818,511 | 6/1974 | Goldberg et al. | 606/153 |
| 3,818,515 | 6/1974 | Neville | 606/153 |
| 4,164,045 | 8/1979 | Bokros et al. | 623/1 |
| 4,224,933 | 9/1980 | Reiling | 128/79 |
| 4,588,461 | 5/1986 | Braun | 156/143 |
| 4,592,341 | 6/1986 | Omagari et al. | |
| 4,699,611 | 10/1987 | Bowden | |
| 4,728,328 | 3/1988 | Hughes et al. | |
| 4,732,152 | 3/1988 | Wallstén et al. | 623/1 |
| 4,852,586 | 8/1989 | Haines | 128/842 |
| 4,863,477 | 9/1989 | Monson | 623/17 |
| 4,955,909 | 9/1990 | Ersek et al. | 623/8 |

FOREIGN PATENT DOCUMENTS

| 146794 | 7/1985 | European Pat. Off. |
| 1103165 | 10/1955 | France |
| 2122032 | 8/1972 | France |
| 2248015 | 5/1975 | France |
| 2391709 | 12/1978 | France |
| 1565828 | 4/1980 | United Kingdom |

OTHER PUBLICATIONS

Copy of International Search Report with annex.
Copy of International Preliminary Examination.

Primary Examiner—David Isabella
Assistant Examiner—Gina M. Gualtieri
Attorney, Agent, or Firm—Sandler Greenblum & Bernstein

[57] ABSTRACT

Tubular endoprosthesis for anatomical conduits is provided with a tubular body having an external surface which includes a plurality of protuberances. Preferably, the protuberances are distributed on the totality of the external surface, and are composed of nipples having a round apex, spaced from each other and radially oriented with respect to the tubular body.

11 Claims, 4 Drawing Sheets

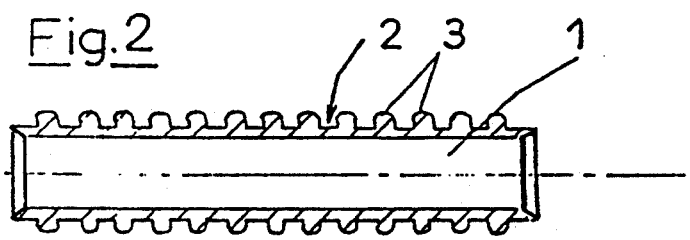
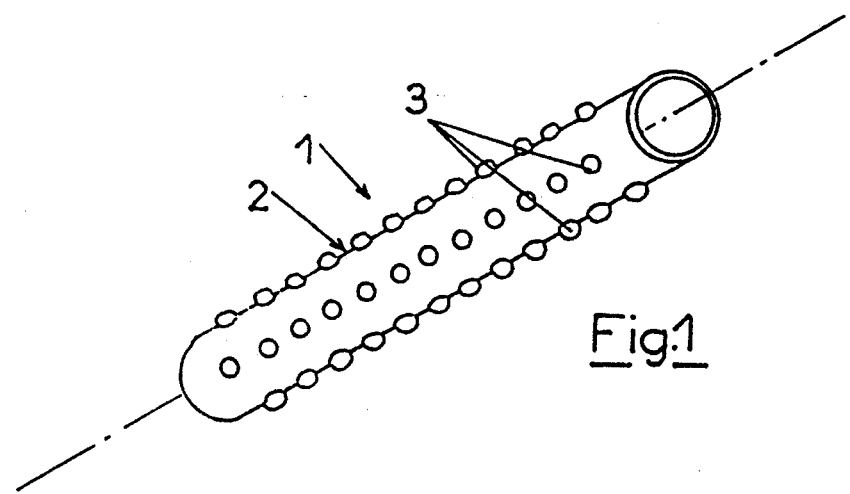
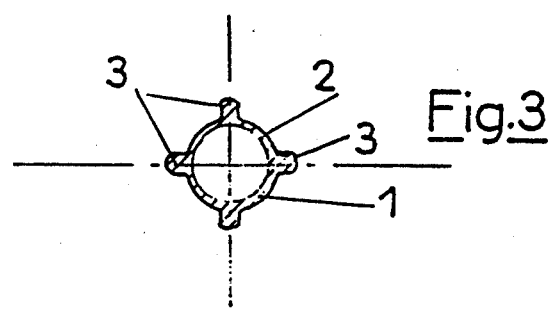

TUBULAR ENDOPROSTHESIS FOR ANATOMICAL CONDUITS

BACKGROUND OF THE INVENTION

1. Field of the Invention

The present invention concerns a tubular endoprosthesis for anatomical conduits or channels. Specifically, particular nonlimiting embodiments of this endoprosthesis are intended to permit the clearance of hardened conduits such as the trachea or bronchus, or to serve as a support for such anatomical conduits when they prove to be weak. Also described is an instrument to put this endoprosthesis in place.

2. Description of Background and Relevant Information

A hollow tube is disclosed in French Patent Document No. 1,130,165 for the treatment of hardening of the esophagus. The device constitutes a flexible tube with a ribbed external surface intended to be installed in a tumoral contraction to permit the passage of food.

This hollow tube has the drawback of not offering any guarantee that it will stay in place, because it can easily turn on itself, which can provoke irritation. Such irritation generates rejection spasms leading to axial shift of the tube, along with the serious consequences to which this shift can lead.

SUMMARY OF THE INVENTION

One of the objects of the present invention is to effectively remedy this serious insufficiency of known endoprostheses.

According to the invention, this objective is obtained by means of an endoprosthesis with a tubular body whose external surface is provided with numerous protuberances or asperities, preferably distributed over the entire surface, or a portion thereof. These protuberances consists of nipples with rounded tops, which are spaced from each other in the longitudinal and peripheral directions on the tubular body, and are preferably radially-oriented.

Another advantage of the endoprosthesis according to the invention is that it can be put easily in place and installs itself in a natural, extremely resistant fashion. In its implantation position, the prosthesis cannot, in effect, turn or slide axially when it is installed in the stenosis. In addition, this prosthesis may be made of a plastic material, such as an elastomer silicone, which is well tolerated by the organism whether healthy or ill, in whom it does not produce rejection spasms or trauma.

In another embodiment of the tubular endoprosthesis according to the invention, the nipples are arranged in lines with spaces in between them and are oriented along the rulings of the tubular body of the endoprosthesis.

The nipples can also be alternatingly distributed on the external surface of the tubular body.

In another embodiment of the tubular endoprosthesis according to the invention, at least one of its ends has an internal slanted wall. Optionally, both or all of its ends may have an internal slanted wall.

The goals, characteristics, and advantages above, and others, will be more apparent from the following description and the attached Figures.

BRIEF DESCRIPTION OF THE DRAWINGS

FIG. 1 is a perspective view of the tubular endoprosthesis according to the invention.

FIG. 2 is a lengthwise cross-section of the tubular endoprosthesis shown in FIG. 1.

FIG. 3 is a transverse cross-section of the tubular endoprosthesis shown in FIG. 2.

DETAILED DESCRIPTION OF THE INVENTION

We refer to the following embodiments to describe the non-limiting construction of this endoprosthesis, as well as the use of instruments permitting its installation.

Figure 5:
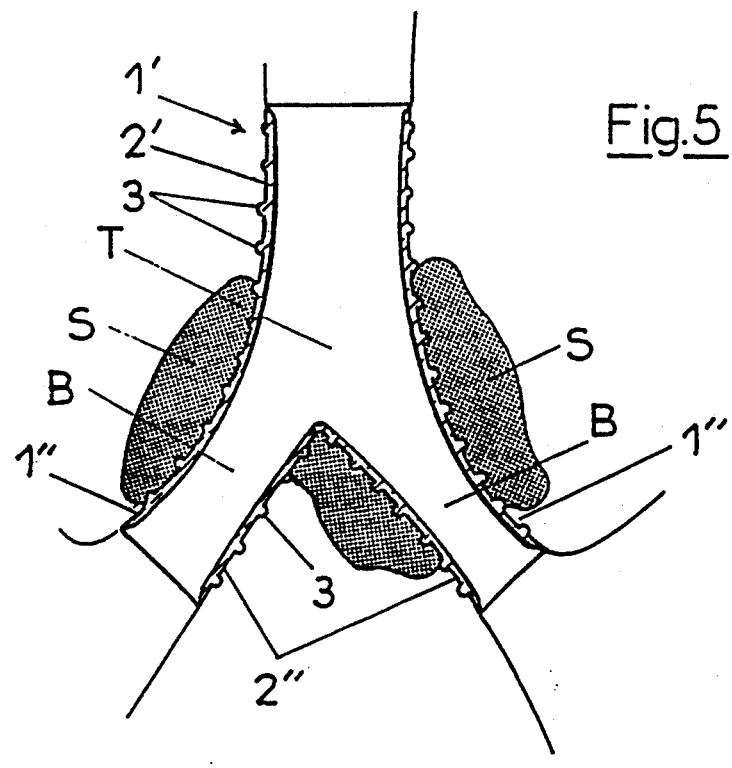
FIG. 5 is a front view of an embodiment of utilizing the endoprosthesis according to the invention, to permit tracheal bronchus clearance.

The tubular endoprosthesis according to the invention can, as a function of the shape of the anatomical conduit or channel inside which it is intended to be installed, affect a variety of shapes. Particular embodiments have a simple rectilinear or essentially rectilinear shape (for example, when it is a tracheal endoprosthesis or bronchus endoprosthesis) as shown in FIG. 1, or a curved shape. Another embodiment has a more complex shape with a principle tube extending into two divergent tubular branches (when it is a trachea bronchus endoprosthesis) as shown in FIG. 5. More precisely, this endoprosthesis can have any shape and any diameter adapted to the shape and the diameter of the conduits, channels or vessels inside which it is to be placed. The endoprosthesis can be made in any supple, semi-rigid, or rigid material, and may be reinforced by an internal reinforcement capable of being well-tolerated by the organism. Preferred embodiments can be advantageously made in a material with an elastic deformation capacity which in a particularly preferred embodiments is an elastomer silicon.

According to one embodiment of the invention, the endoprosthesis has a tubular body 1 with an external surface 2, which is intended to come into contact with the internal wall of an anatomical conduit. External surface 2 is provided with numerous protuberances or asperities 3, which may be distributed evenly over the entire external surface 2 or positions thereof.

These protuberances or asperities 3 can have very different shapes, without edges that could injure the anatomical walls with which they are supposed to come into contact. In a preferred embodiment the proterberances or asperities 3 consist of nipples with rounded tops, arranged in lines oriented according to the rulings of the endoprosthesis; these lines of nipples can be angularly spaced, as shown particularly in FIG. 1. These nipples 3 are radially-oriented in relation to the tubular body 1, and they are spaced from each other in the lengthwise direction as well as the peripheral direction.

They can be advantageously distributed alternately on the lateral surface of the tubular body 1. The nipples can have a circular or any other shaped section. Also, these nipples or nibs 3 are ineffaceable, that is, they are sufficiently rigid so that they don't compress, bend, or retract under the conditions of use.

Figure 4:
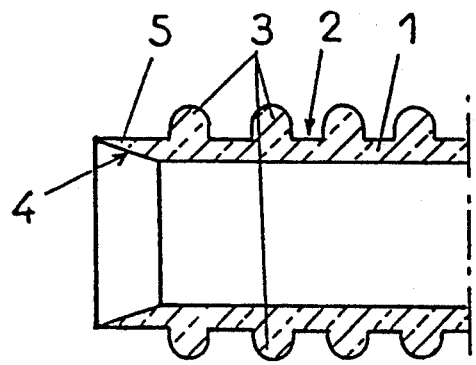
FIG. 4 is an enlarged view, in detail, of a lengthwise cross-section of one of the ends of the endoprosthesis.

At least one, and preferably both ends, of the endoprosthesis are provided with an internal sloping edge 4 (FIG. 4), so that the ends consist of thin, tapered lips. This feature provides that when the endoprosthesis is in place, it forms no retention asperity favoring the formation of diverse accumulations as a function of the nature of the conduits, channels or vessels, at the entry or exit of the prosthesis.

The alternative embodiment of the prosthesis illustrated in FIG. 5 differs from the preceding only by its slightly more complex shape adapted to the conformation of the conduits in which it is to be installed. According to this variation of construction, the prosthesis includes a principal tubular body 1' extended by two divergent tubular branches 1"; the external surfaces 2', 2" of the main body and of the branches are provided with nipples 3, as previously described. Such a prosthesis is intended to be placed at the branching point of an anatomical conduit. According to a very interesting application, such a prosthesis is intended to constitute a tracheobronchus endoprosthesis, allowing the conduit to remain open despite an obstruction S affecting both the internal part of the trachea T and the initial portion of the two bronchi B to be by-passed.

Figure 12:
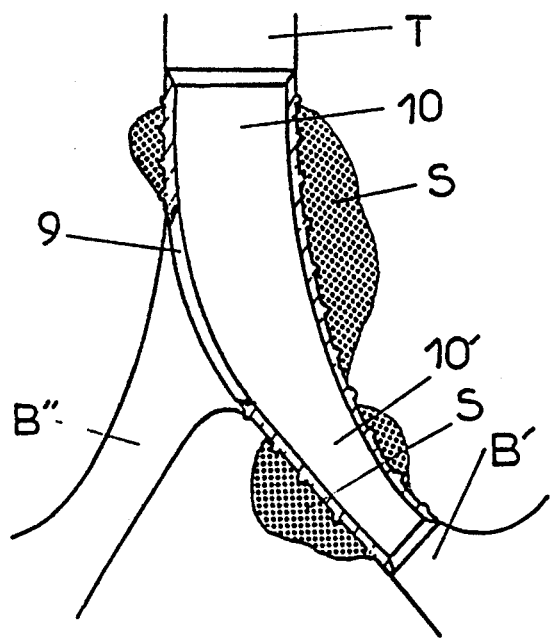
FIG. 12 is a front view of another embodiment of a tracheal bronchus endoprosthesis according to the invention.

FIG. 12 shows another embodiment of a prosthesis according to the invention such as a tracheobronchus endoprosthesis, also intended to be placed at the branching point of an anatomical conduit, such as in the case of an obstruction S to be by-passed affecting only the base of the major conduit (trachea T, for example) and only one of the branches (one of the bronchi B', for example). In this case, the prosthesis has a curved shape and includes a major part 10 extended by a second part of smaller diameter 10'. In addition, it has an opening 9 laterally placed at the juncture point of the major part 10 and secondary part 10', the opening 9 is intended to be placed at the entry of a second healthy branch of an anatomical conduit (the other bronchus B", for example), in order to permit a passage between the principal conduit T and a healthy branch B".

The lateral opening 9 can also allow and favor the installation of a second independent tubular branch similar to the secondary part 10', in order to create an endoprosthesis like the one shown in FIG. 5.

Figure 6:
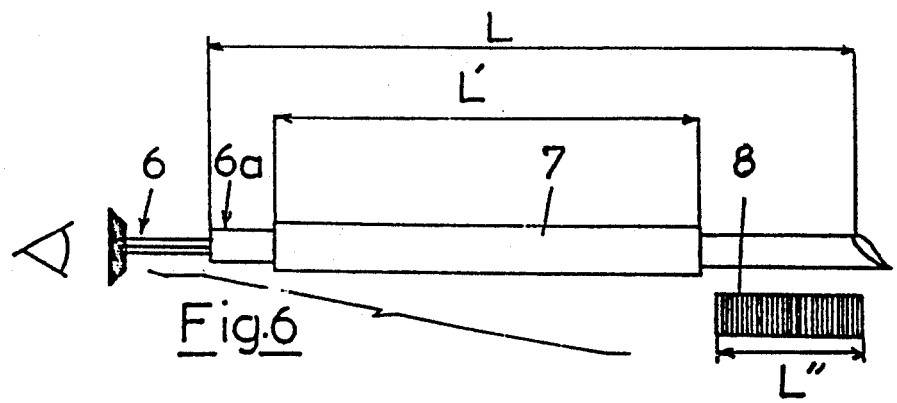
FIG. 6 is a view of the instruments permitting the placement of an endoprosthesis like the one illustrated in FIGS. 1-4.
Figure 7:
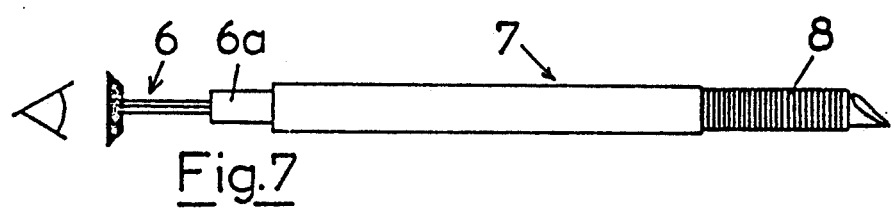
FIGS. 7-11 show the operation of the placement instrument shown in FIG. 6 and the installation method for the tubular endoprosthesis according to the invention.
Figure 8:
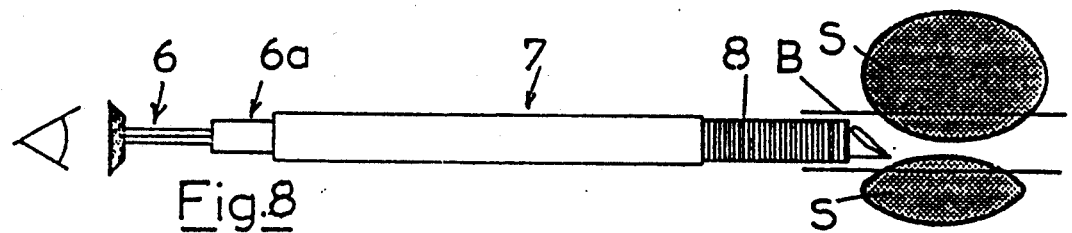
Figure 9:
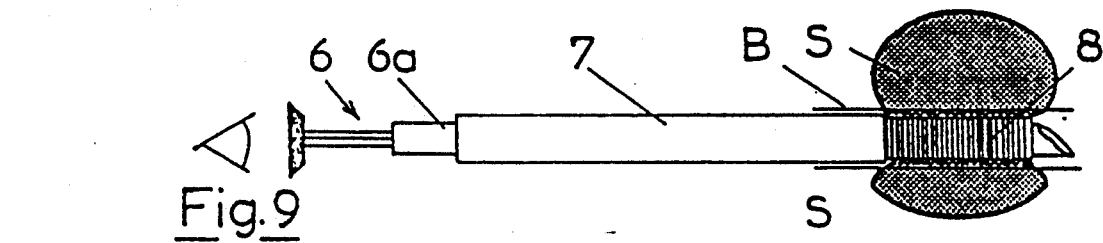

We have shown in FIG. 6 an installation or introduction instrument for endoprosthesis consisting of a rectilinear or essentially rectilinear tube such as those which are intended to be installed in the trachea or in the weak, hardened or tumor-compressed bronchi, in order to serve as their support or to permit them to be cleared.

This instrument includes a classic bronchoscope 6 on the elongated cylindrical body or guidance rod 6a, on which is mounted, with a sliding ability in relation to said rod, a tubular pusher 7 whose length L' is less than the length L of the guidance rod 6a. The difference in length between the rod 6a of the bronchoscope and the pusher 7 corresponds at least to the length L" of the endoprosthesis 8 intended to be introduced and positioned with the help of the instrument; this difference in length (L—L') being, however, preferably greater than the length L' of the endoprosthesis.

FIGS. 7-11 show the installation procedure of a simple endoprosthesis 8 in an anatomical conduit B (for example, trachea or bronchus) obstructed by a compressive tumor S.

The endoprosthesis 8 is first placed around the end of the rod 6a of the bronchoscope 6, in front of the pusher 7 (FIG. 7), the tapered end of the rod emerging at the front of the endoprosthesis, in order to facilitate its progress in the anatomical conduit.

The rod furnished with endoprosthesis 8 is then introduced and driven into the anatomical conduit B (FIG. 8) until said endoprosthesis reaches the desired position (FIG. 9), that is, the place where the hardening or compressive tumor is located.

Figure 10:
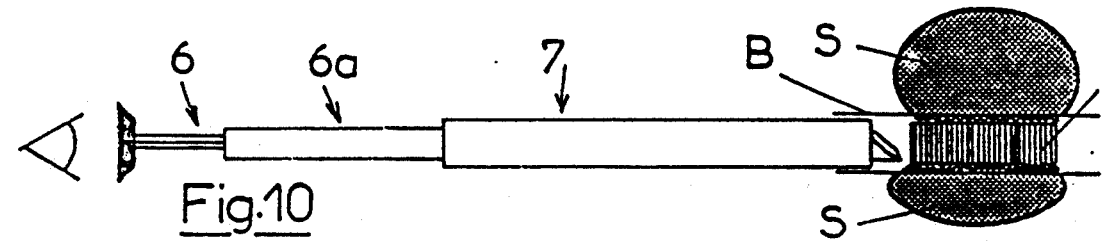
Figure 11:
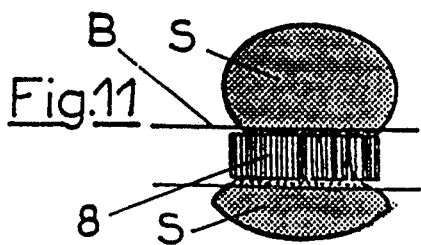

The rod 6a of the bronchoscope is then withdrawn while maintaining the pusher 7 in place, which prevents any backwards movement of the endoprosthesis during this withdrawal (FIG. 10). Finally, the pusher is withdrawn, the endoprosthesis then being installed and solidly fixed in its lodging because of the nipples provided on its external surface, on which the surrounding anatomical wall exerts pressure preventing any shift or movement of the endoprosthesis.

I claim:

1. Tubular endoprosthesis for anatomical conduits, comprising:
    a biocompatible tubular body composed of a semi-rigid or rigid material having an external surface and two open ends forming a passage therethrough, said body adapted to contact an internal wall of the anatomical conduit; and
    means forming a plurality of discrete protuberances distributed on said external surface for maintaining said tubular body within said anatomical conduit against return or axial displacement without injuring the internal wall of the anatomical conduit; and
    said means forming a plurality of protuberances comprising ineffaceable nipples having rounded tops, with said nipples being spaced along the length and periphery of said external surface of said tubular body.

2. The tubular endoprosthesis according to claim 1, wherein said nipples are radially oriented with respect to said tubular body.

3. The tubular endoprosthesis according to claim 1, wherein said nipples having rounded tops are distributed over substantially the entire external surface of said tubular body.

4. The tubular endoprosthesis according to claim 1, wherein said nipples are arranged in lines which are spaced from each other along said length of the external surface.

5. The tubular endoprosthesis according to claim 4, wherein said lines are positioned along rulings of said tubular body.

6. The tubular endoprosthesis according to claim 5, wherein said nipples are alternately distributed along said tubular body.

7. The tubular endoprosthesis according to claim 1, wherein said semi-rigid or rigid material comprises a material having elastic deformation ability.

8. The tubular endoprosthesis according to claim 7, wherein said material is an elastomeric silicone.

9. The tubular endoprosthesis according to claim 1, wherein said tubular body includes a lateral opening adapted to maintain a passage between an anatomical conduit in which the tubular endoprosthesis is positioned and a branch thereof.

10. Tubular endoprosthesis for anatomical conduits, comprising:
   a biocompatible tubular body having an external surface, wherein said tubular body includes two open ends, and at least one of said two ends has an internal slanted wall; and
   means forming a plurality of protuberances distributed on said external surface for maintaining said tubular body in an anatomical conduit without injuring anatomical walls of the anatomical conduit; and
   said means forming a plurality of protuberances comprising nipples having rounded tops, with said nipples being spaced along the length and periphery of said external surface of said tubular body.

11. The tubular endoprosthesis according to claim 10, wherein each of said two ends has an internal slanted wall.

* * * * *

UNITED STATES PATENT AND TRADEMARK OFFICE
CERTIFICATE OF CORRECTION

PATENT NO. : 5,236,446
DATED : August 17, 1993
INVENTOR(S) : J. DUMON

It is certified that error appears in the above-indentified patent and that said Letters Patent is hereby corrected as shown below:

At column 1. line 40 of the printed patent, change "consists" to ---consist---.
At column 4, line 35 (claim 1, line 11) of the printed patent, change "return" to ---turning---.

Signed and Sealed this

Fifteenth Day of November, 1994

Attest:

BRUCE LEHMAN

Attesting Officer     Commissioner of Patents and Trademarks